(12) United States Patent
Polidoro (10) Patent No.: US 7,001,361 B2
(45) Date of Patent: Feb. 21, 2006

(54) BLUNTING DEVICE FOR A HOLLOW MEDICAL NEEDLE

(75) Inventor: John M. Polidoro, Coventry, CT (US)

(73) Assignee: Medical Engenuity LLC, Coventry, CT (US)

( * ) Notice: Subject to any disclaimer, the term of this patent is extended or adjusted under 35 U.S.C. 154(b) by 384 days.

(21) Appl. No.: 10/226,399

(22) Filed: Aug. 23, 2002

(65) Prior Publication Data
US 2003/0040710 A1 Feb. 27, 2003

Related U.S. Application Data

(60) Provisional application No. 60/314,881, filed on Aug. 24, 2001.

(51) Int. Cl.
*A61M 5/178* (2006.01)
(52) U.S. Cl. .............................. 604/164.06; 604/164.01
(58) Field of Classification Search .......... 604/164.01, 604/164.05, 168.01, 158, 170.01, 198, 164.06; 606/213; 600/567
See application file for complete search history.

(56) References Cited

U.S. PATENT DOCUMENTS

| | | | | |
|---|---|---|---|---|
| 4,627,841 A | * | 12/1986 | Dorr | 604/158 |
| 4,827,941 A | * | 5/1989 | Taylor et al. | 600/434 |
| 5,113,872 A | * | 5/1992 | Jahrmarkt et al. | 600/585 |
| 5,117,838 A | * | 6/1992 | Palmer et al. | 600/585 |
| 5,271,415 A | * | 12/1993 | Foerster et al. | 600/585 |
| 5,312,345 A | * | 5/1994 | Cole | 604/110 |
| 6,106,499 A | * | 8/2000 | Overton et al. | 604/170.01 |
| 6,475,189 B1 | * | 11/2002 | Lilley, Jr. | 604/164.01 |

* cited by examiner

*Primary Examiner*—Manuel Mendez
(74) *Attorney, Agent, or Firm*—McCormick, Paulding & Huber LLP (57) ABSTRACT

A blunting device for use with a hollow needle having an exit end with a sharp edge for penetrating a body. The blunting device having a coupler for connection to, or is coupled to, an insert device whereby upon removal from, or insertion depending upon the specific insert device, the needle is blunted. The blunting device is also capable of operation with a hollow needle that has not been modified to specifically receive the blunting device.

16 Claims, 5 Drawing Sheets

BLUNTING DEVICE FOR A HOLLOW MEDICAL NEEDLE

CROSS-REFERENCE TO OTHER APPLICATIONS

This application claims priority to U.S. Provisional Application No. 60/314,881 filed Aug. 24, 2001, entitled "Safety Needle Apparatus Comprised of a Needle Assembly and a Device Containing a Detachable Safety Feature," the entire disclosure of which is incorporated herein by reference.

FIELD OF THE INVENTION

The present invention generally relates to medical devices, and more particularly to a blunting device for use with a hollow medical needle having a bevel pointed exit end for penetrating a body. The blunting device prevents unintentional needle puncture trauma to the user or another.

BACKGROUND OF THE INVENTION

Hollow Medical needles can be broadly classed as needles for the introduction of fluids into or removal of fluids from a body, or needles that act as conduits for guiding insert devices into a body. Insert devices include but are not limited to guide wires, stylets, obturators, optical devices, video devices, and endoscopes. A hollow Medical needle typically has an exit end terminated by a beveled pointed end defining a sharp edge designed to penetrate a body, such as the flesh of an animal. While an unused needle presents an unintentional puncture trauma hazard to a user or another, a used needle presents not only a puncture hazard but also a means for transmitting disease.

Medical needles for intravenous insertion are particularly susceptible to becoming contaminated with blood borne diseases such as HIV, Hepatitis B, and Hepatitis C. Consequently, many state and federal laws and regulations deal with the handling and disposal of such used needles.

Healthcare workers are particularly vulnerable to contamination from unintentional puncture trauma in handling needles after use and until proper disposal thereof. Unintentional puncture trauma can occur in numerous ways, such as in handing a used needle to another person or reaching for an item and contacting a used needle that has not yet been safely discarded.

Most prior art needle blunting devices, while designed to blunt used needles, do not protect healthcare workers for the entire time from termination of use to disposal. Such blunting devices are generally designed for insertion into a needle after it has been used. This procedure requires that the used needle be withdrawn, a blunting device obtained, and thereafter inserted into the used needle. In the case of a needle that functions as a conduit for an insert device, the needle is blunted by the insert device while the insert device is positioned therein, but it is "unblunted" after the insert device is removed and until a blunting device is installed. Consequently, there is a period when a used needle posses a hazard.

Medical needles also pose a potential unintended puncture trauma hazard to the body into which the needle is inserted, while inserted therein. For example, a needle once properly positioned in a vein, can unintentionally puncture the vein if inadvertently moved. This is a common concern in procedures where needles are used to provide passageways for insert devices. The needle presents a hazard until the insert device is inserted and the needle is blunted thereby. However, when one insert device is removed to be replaced by another insert device, the needle point is exposed during the interval between removal of the first insert device and insertion of the second.

Further, blunting devices are designed for use in conjunction with needles specifically designed to receive them. In other words, the blunting device and the needle are an integral system and must be used together. A blunting device for one particular design of needle will not work properly with another needle of a different design or visa versa.

Based on the foregoing, it is an object of the present invention to develop a needle blunting device that acts in conjunction with an insert device thereby eliminating, or substantially reducing, the time a used needle is not blunted.

Another objective of the present invention is to develop a blunting device for a needle that will blunt a needle in use after removal of an insert device from the needle.

It is a further object of the present invention to develop a blunting device for a needle that does not require alteration or special design of the needle with which it is used.

SUMMARY OF THE INVENTION

According to the present invention, a blunting device for a needle has a stopper connected to a blunting piece. The blunting device is inserted into a needle having a bore with an entrance end and an exit end wherein the exit end has a sharp edge defining a point for penetrating a body. The blunting piece is inserted into the entrance end and is sized to pass through the bore positioning a portion of the blunting piece in the exit end. The stopper is sized such that it cannot pass through the bore when entering from the entrance end. A catch is operatively associated with the stopper and the blunting piece to position the portion of the blunting piece within the exit end and prevent retrograde movement of the blunting piece. The catch is designed to actuate upon exiting the exit end of the needle.

The present invention provides considerable utility for blunting a needle that has not been specifically modified to receive a blunting device. The catch secures the position of the blunting piece, at least as to one direction of axial movement in the bore, by acting against the sharpened end of the needle. The stopper secures the position or at least limits movement of the blunting piece in the other axial direction. With this blunting device, the needle need only be designed with the penetration function of the sharp end in mind. No consideration needs to be given to how the sharp end will interact with the catch. In addition, the stopper takes advantage of the normal shape of the needle hub bore, which is usually frustoconical. Thus, the blunting device can be used with all needles of similar dimensions.

As an additional feature, the blunting device may have a coupler to receive an insert device. The coupler releasably secures the insert device to the blunting device such that the insert device may be used to draw, or push, the blunting device into and through the needle after which the insert device may be uncoupled from the blunting device permitting disposal of only the needle with blunting device.

In another embodiment of the present invention, a blunting device for a needle has a stopper connected to a blunting piece. The blunting device is inserted into a needle having a bore with an entrance end and an exit end wherein the exit end has a sharp edge for penetrating a body. The blunting piece is inserted into the entrance end and is sized to pass through the bore and a portion of the blunting piece positioned therein. The stopper is sized such that it cannot pass through the bore when entering from the entrance end. A coupler operatively associated with the stopper and the blunting piece permits an insert device to be attached to the blunting device.

In yet another embodiment of the present invention, a blunting device for a needle has a stopper connected to a blunting piece. The blunting device is inserted into a needle having a bore with an entrance end and an exit end wherein the exit end has a sharp edge for penetrating a body. The blunting piece is inserted into the entrance end and is sized to pass through the bore and a portion of the blunting piece positioned therein. The stopper is sized such that it cannot pass through the bore when entering from the entrance end. An insert device is operatively associated with the stopper and the blunting piece but may be disassociated from the stopper and blunting piece.

The prior two embodiments may also include a catch associated therewith to assist in retaining a portion of the blunting piece within the exit end. The catch can be of almost any design including but not limited to catches that actuate upon exiting the exit end, catches that are associated exclusively with the blunting device that provide frictional or grabbing methods of holding, or catch systems that have one part on the blunting device and a second part on the needle.

An advantage of the prior two embodiments is that the blunting device is, or may be, associated with an insert device. Therefore, the insert device may be used to draw, or push, the blunting device into the needle assuring continuous blunting of the used needle, by either the insert device or the blunting device.

BRIEF DESCRIPTION OF THE DRAWINGS

FIG. 8A-E is a series of fragmentary side elevational views of couplers that can be employed for coupling an insert device to a blunting device.

DETAILED DESCRIPTION OF THE PRESENT INVENTION

Figure 1:
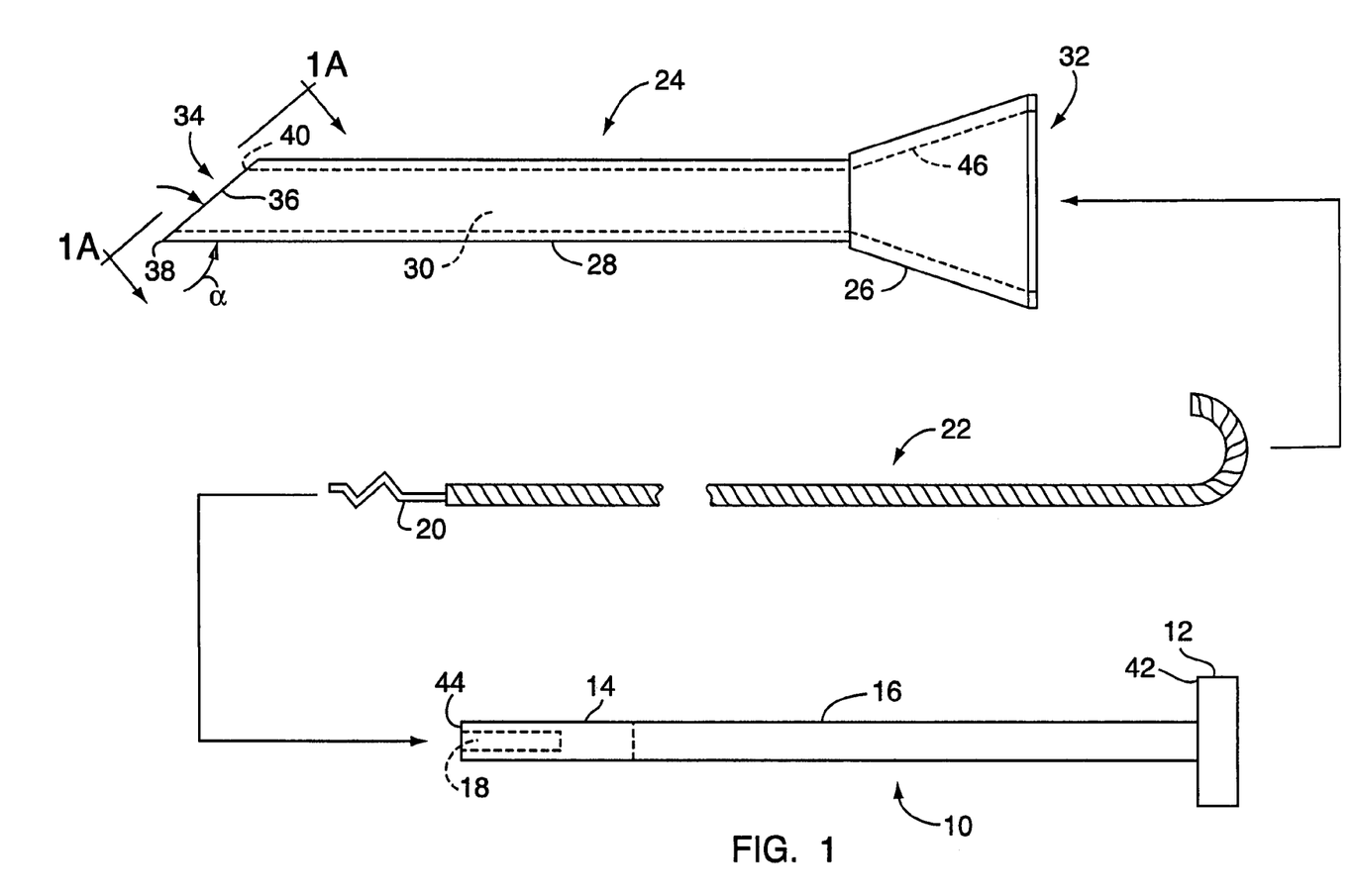
FIG. 1 is an exploded side elevational view of a blunting device embodying the present invention shown in a conjunction with a guide wire and a needle.
Figure 1A:
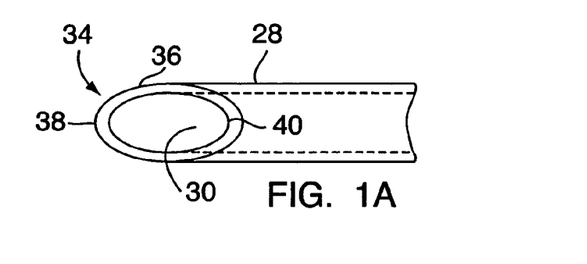
FIG. 1A is a somewhat enlarged fragmentary view of the needle as viewed along the line 1A—1A of FIG. 1.

As shown in FIG. 1, a blunting device, generally referred to by reference number 10, comprises a stopper 12 connected to a blunting piece 14 by a connecting member 16 (the dotted line being the point of demarcation). The blunting piece 14 has a blind bore 18 designed to act as a coupler to receive a coupling portion 20 of a flexible guide wire 22. The guide wire 22 is designed to be inserted into a hollow needle, generally denoted by the reference number 24. The needle has a hub 26 connected to a cannula 28 which define a bore 30 through the needle 24 having an entrance end 32 and an exit end 34. The portion of the bore 30 within the hub 26 is generally frustoconical. Referring to FIGS. 1 and 1A, the exit end 34 has a sharp peripheral edge 36 designed for penetrating a body (not shown).

The stopper 12 has a cross-section that prevents it from passing through the bore 30 when entering the bore from the entrance end 32. The cross-section of the stopper 12 is designed such that stopper can enter the entrance end 32 and be stopped from passing through the bore 30 at some location within the hub 26. The cross-section of the stopper 12 could be, however, of such a size as not to allow the stopper to enter the entrance end 32. In addition, if the cannula 28 does not have a generally cylindrical bore 30, the stopper 12 could have a cross-section that causes the stopper to stop at a location in the cannula.

The blunting piece 14 has a cross-section that permits it to enter the bore 30 through the entrance end 32 pass through the bore 30 and exit the bore through exit end 34. Preferably, the cross-section of the blunting piece 14 is sized in close tolerance to the cross-section of the bore 30 within the cannula 28 and at the bore exit end 34. Optimally, the tolerance is such that the blunting piece 14 has sufficient clearance to slide within the bore. It is desired that the blunting piece 14 have a cross-section that holds the blunting piece substantially coaxially within the cross-section of the bore at the exit end 34.

The stopper 12 and the blunting piece 14 are coupled by a member 16, which cooperates with the blunting piece and stopper to place a portion of the blunting piece within the exit end 34. The exit end 34 has an outer peripheral edge 36 that is at a rake angle or bevel α relative to the bore axis. Referring to FIG. 1A, the rake angle α defines a point or tip 38 some distance from a heal 40. Ideally the blunting piece 14, has a length at least as long as the linear distance from the tip 38 to the heal 40. Additionally, the length of the blunting device 10 from a point of engagement 42 of the stopper 12, which is the point at which the stopper first engages a surface 46 of the frustoconical portion of the bore 30, to a distal end 44 of the blunting piece 14 must be such that when the blunting device 10 is positioned in the bore 30 and the point of engagement 42 contacts the interior surface 46 of the bore, the distal end 44 extends to at least the tip 38, but preferably outwardly from the bore exit end 34 past the tip 38. The stopper 12 may also assist in decoupling the insert device 22 from the blunting device 10 by preventing longitudinal movement of the blunting device 10 in the bore 30.

It should be readily appreciated that the blunting piece 14 can be of almost any length to permit the use of the blunting device 10 with different needles having approxiamtely the same bore cross-sectional characteristics, but different lengths. In addition, if the blunting piece 14 is of sufficient length, the blunting device 10 could be used with needles of differing hub cross-sectional bore characteristics, because it is unnecessary for the stopper to enter the hub.

The various elements of the blunting device 10 can be made from any suitable material including but not limited to plastic and metal. While the blunting device has been described as comprising at least three elements, the three elements can be manufactured and assembled in any number of ways. For example, the three elements may be separately manufactured and attached or certain elements may be a single piece, such as described above for the blunting piece 14 and the connecting member 16.

While a guide wire insert device has been depicted, the invention should not be considered so limited. Other insert devices such as stylets, obturators, optical devices, video devices, and endoscopes are considered within the scope of the invention.

Figure 2:
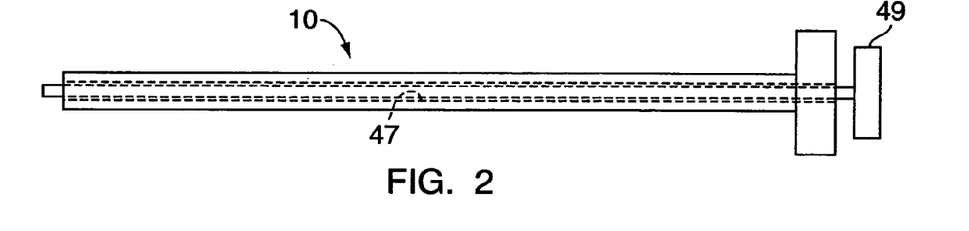
FIG. 2 is a side elevational view of an alternate configuration of the blunting device depicted in FIG. 1.

As shown in FIG. 2, the coupler may comprise a through bore 47 instead of the blind bore 18. In this configuration, a blunting device 10 can be placed onto a stylet 49, or other similar insert device, before the insertion into the needle 24. Unlike the prior configuration where the insert device draws the blunting device 10 into the needle 24, the insert device pushes the blunting device into the needle. The used needle 24 with blunting device 10 positioned therein can be withdrawn from the body along with the insert device, or after the insert device has been removed.

Figure 3:
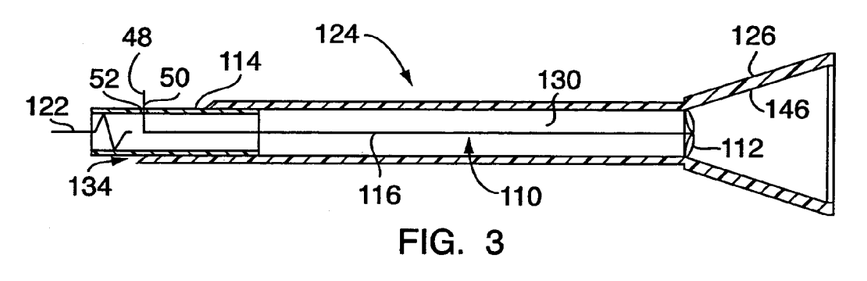
FIG. 3 is a longitudinal section view of a needle shown with another blunting device secured in a blunting position therein.

FIG. 3 illustrates a second embodiment of the present invention. As this blunting device is similar in many respects to the blunting device previously described, like reference numerals preceded by the number 1 are used to indicate like elements. In this embodiment, the blunting device 110 comprises a stopper 112 coupled by a member 116 to a blunting piece 114 and a retaining member or catch 48 that can project radially outwardly from the blunting piece 114.

The blunting piece 114 is a hollow cylinder with a diameter sufficient to permit the blunting piece to slide within the bore 130. The hollow cylinder acts as a coupler to accept a portion of an insert device, holding the latter portion by frictional engagement with the inside surface of the hollow cylinder.

The member 116 is flexible and subject to column buckling, being made from wire. The stopper 112 comprises a portion of the wire from which the member 116 is made twisted to define a cross-section larger than the cross-section of the wire itself and which is incapable of passing through the bore 130.

The catch 48 is formed by passing the distal end 50 of the member 116 through a hole 52 defined by the blunting piece 114. As this embodiment has a member 116 that does not resist column buckling, the blunting device 110 is drawn through the bore 130 by an insert device to which it is attached. In operation, when the blunting piece 114 is drawn into the bore 130 the distal end 50 of the member 116 is forced into the blunting piece. The member 116 acts as a cantilever spring to exert radially outwardly directed biasing force upon the distal end 50 to cause it to project radially outwardly from the blunting piece 114 whenever possible. As the distal end 50 emerges from the bore 130 upon passing through the needle exit end 134, the energy stored within the resilient spring wire member 116 forces the distal end to move radially outwardly from the blunting piece 114, such that a projecting portion 52 of the member 116 acts as a catch. The catch 48 and the stopper 112 operatively cooperate to position fixedly a portion of the blunting piece 114 in the needle exit end 134.

Where the blunting device 110 relies on the cooperation of a catch 48 and a stopper 112 to position fixedly the blunting piece 114 in the exit end 134, thereby blunting the exit end 134, in determining the required length of the blunting piece one must consider the distance between the catch and the stopper in relation to the length of the needle into which it is inserted. If the distance from the stopper 112 to the catch 48 is approximately equal to the distance from the point at which the stopper will contact the needle 110 and the point at which the catch 48 will activate upon exiting the exit end 134 of the needle 110, the length of the blunting piece may be approximately equal to the distance from the tip 30 to the heal 40 (See FIG. 1A). However, if the length from the contact point of the stopper 112 with the needle 110 and the point at which the catch 48 will activate upon exiting the exit end 134 of the needle is shorter than the distance from the stopper to the catch, the length of the blunting piece 114 will have to be such as to compensate for this difference.

Figure 4:
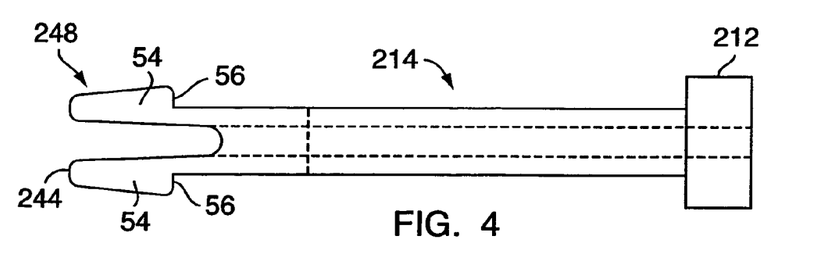
FIG. 4 is a side elevational view of a third blunting device of the present invention.

FIG. 4 shows a third embodiment of the present invention. As this blunting device is similar in many respects to the blunting device described above, like reference numerals preceded by the number 2 are used to indicate like elements. Similar to the embodiment depicted in FIG. 3, this embodiment incorporates a resilient catch 248 designed to deploy upon exiting the exit end 34 (see FIG. 1) of a needle. The catch 248 comprises a pair of diametrically opposed prongs 54. Each prong 54 has a latching surface 56 to engage the sharp peripheral edge 36 of the needle 24. It is understood that if the inner peripheral edge has a rake, only one surface may engage the perimeter. The blunting piece 214 begins at the distal end 244 and extends back toward the stopper 212.

The resilient prongs 54 act as cantilevered springs. Referring to FIG. 1, during operation the catch 248 enters the bore 30 from the entrance end 32. The prongs 54 are cammed radially inwardly from a projected position to a retracted position such that the prongs can pass through the bore 30. Upon exiting the bore 30 through the exit end 34, the prongs 54 are resiliently biased toward the projected position.

While two types of retention devices or catches that deploy upon exiting a bore have been depicted, the invention should not be considered so limited. Retention devices of other well known types, such as a spring ball, may be employed and are considered to be within the scope of the invention.

Figure 5A:
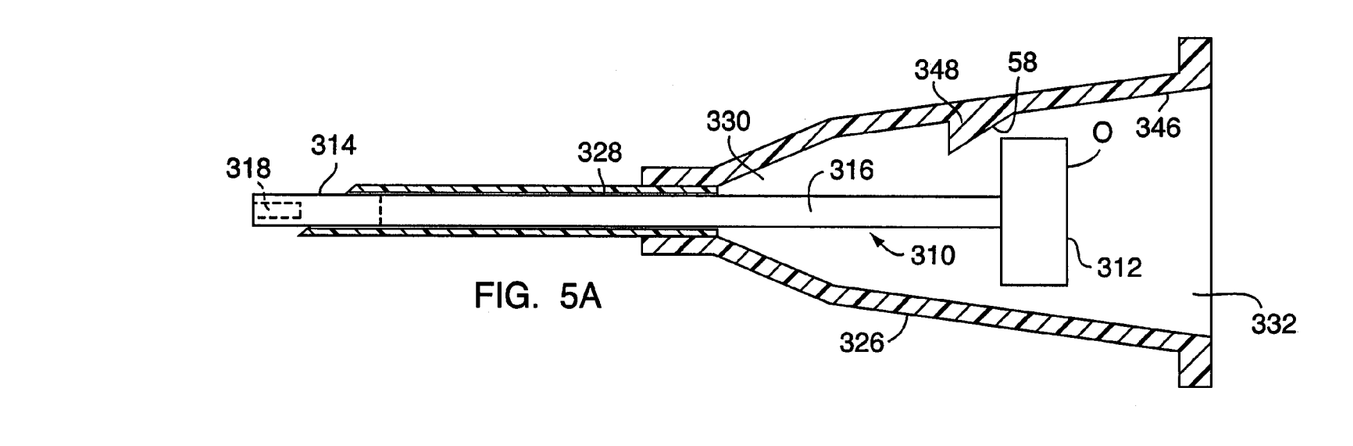
FIG. 5A is a longitudinal sectional view of a fourth embodiment of the present invention.
Figure 5B:
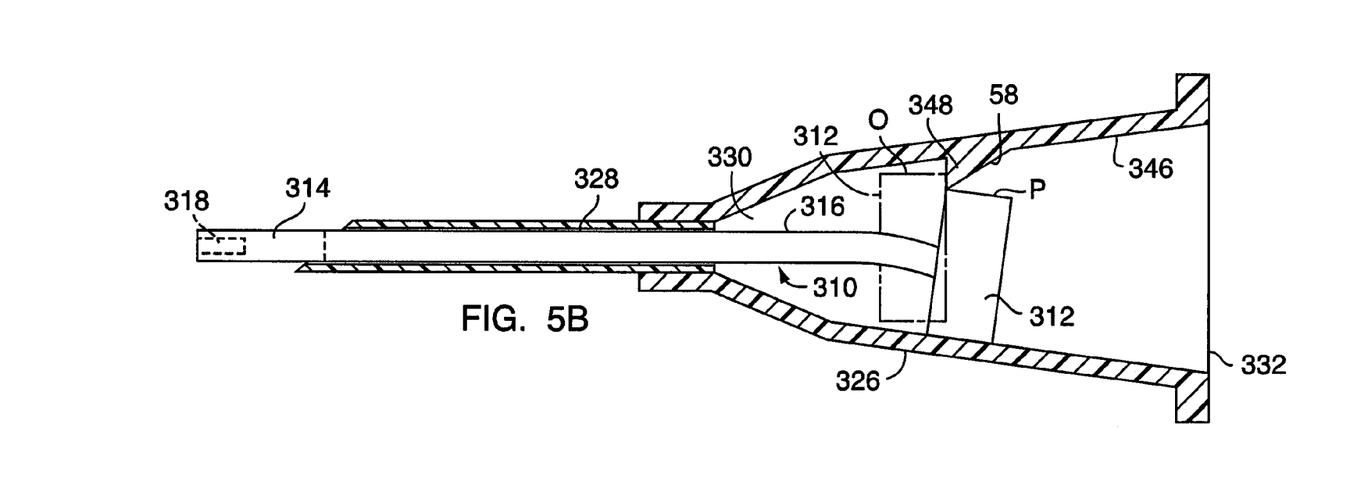
FIG. 5B is similar to FIG. 5A but shows the stopper in a latch cam engaging position.

FIGS. 5A and B depict a fourth embodiment of the present invention. As this blunting device is similar in many respects to the blunting device described above, like reference numerals preceded by the number 3 are used to indicate like elements. In this embodiment, the catch 348 comprises a cam latch 58 projecting outwardly from the inner wall 346 of the bore 330. The blunting piece 314 has a blind bore 318 for coupling the portion of an insert device to the blunting device 310. As the blunting device 310 enters the bore 330 through the entrance end 332, the stopper 312 encounters a cam surface on the cam latch 58. As shown in FIG. 5B, the resilient member 316 acts as a cantilever spring such that the member deflects from its normal position O to a deflected position P as the stopper 312 passes over the cam latch 58 and is then resiliently biased to its normal position after passing the latch. As the member 328 resists column buckling, the blunting piece 314 is secured in position by the stopper 312 that is fixedly positioned longitudinally in the hub 326 by contact with the interior surface 346 and the latch 58.

Figure 6A:
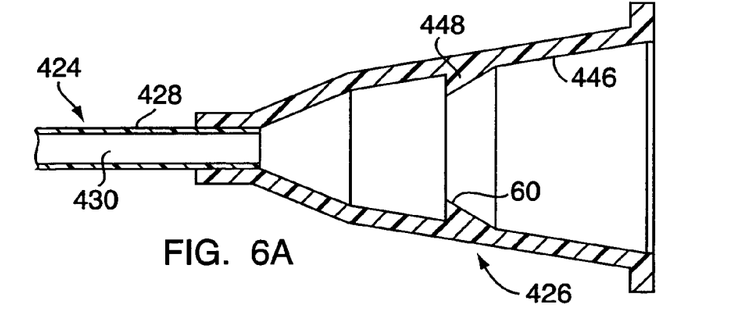
FIG. 6A is a longitudinal sectional view of a portion of another needle.
Figure 6B:
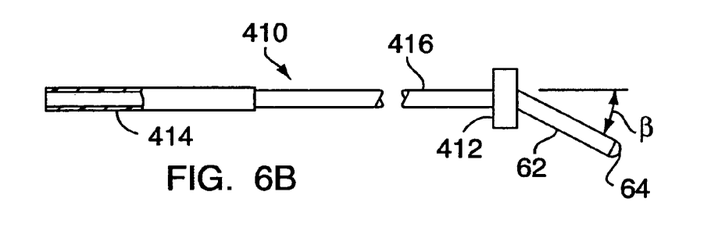
FIG. 6B is a side elevational view of a blunting device for use with the needle of FIG. 6A.
Figure 6C:
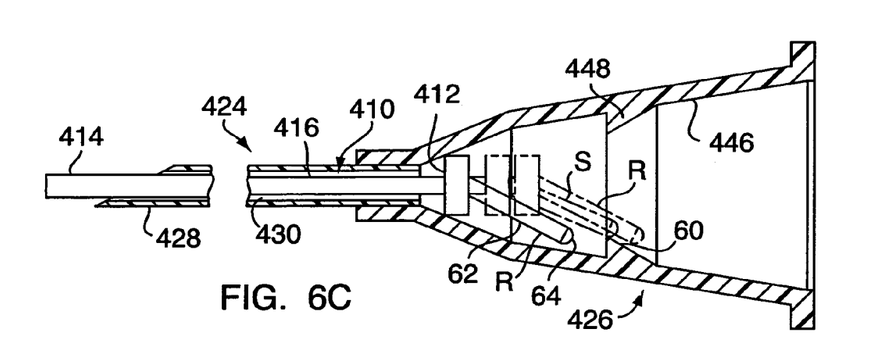
FIG. 6C is similar to FIG. 6A, but shows the blunting device of FIG. 6B latched in blunting position with the needle.

FIGS. 6A, B, and C depict a fifth embodiment of the present invention. As this blunting device is similar in many respects to the blunting device described above, like reference numerals preceded by the number 4 are used to indicate like elements. This embodiment like the fourth embodiment employs a catch 448 wherein a portion of the needle 424 is modified. The interior surface 446 of the needle hub 426 has an annular cam latch keeper 60 defined by a frustoconical portion of the hub. The frustoconical bore portion converges in the direction of the needle exit end and defines part of catch 448. Cantilevered at an angle $\beta$ relative to the member is a latch pawl 62 having a distal end 64. In operation, the blunting device 410 is drawn or passed through the bore 430 such that the member 416 acts like a resilient cantilever spring causing the pawl 62 to deflect from an original position R to a deflected position S to ride over the flange 60 and then be deflected back toward its original position. As the member 428 resists column bucking, the blunting piece 414 is held in position by the stopper 412 engaging the inner surface 446 and the distal end 64 engaging the flange 60.

Figure 7:
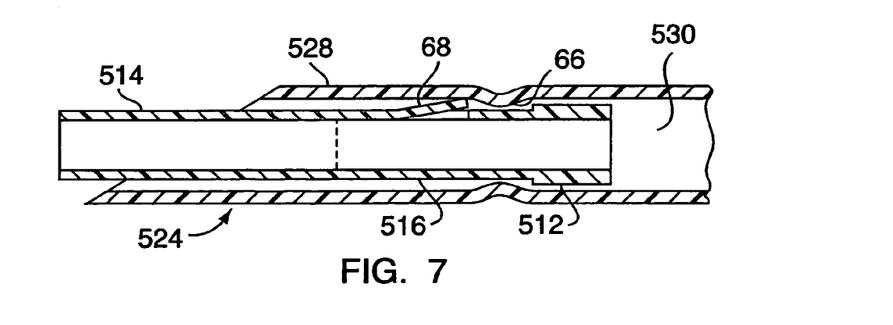
FIG. 7 is a side elevational view of another type of catch for use the blunting device.

FIG. 7 depicts a sixth embodiment of the present invention. As this blunting device is similar in many respects to the blunting device described above, like reference numerals preceded by the number 5 are used to indicate like elements. In this embodiment, the cannula 528 has an interior surface that defines a protrusion 66. The stopper 512 has a cross-section that is larger than the cross-section of the cannula 528 in the area of the protrusion 66 such that the stopper 512 cannot pass through the bore 530. A resilient pawl 68, which acts like a cantilever spring, projects outwardly from the member 516. The pawl 68 deflects as it passes over the protrusion 66. As with the fifth embodiment, the member 516 resists column buckling, thus the stopper 512 and the pawl 68 and protrusion 66 cooperate to hold the blunting piece 514 in a longitudinally fixed position within the exit end of the needle 524.

Figure 8A:
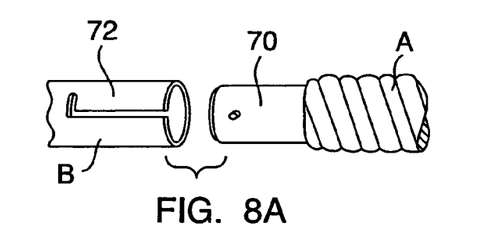
Figure 8B:
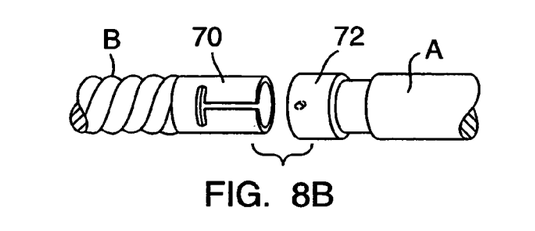
Figure 8C:
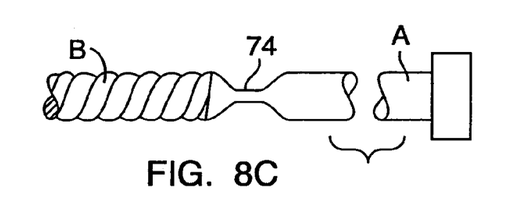
Figure 8D:
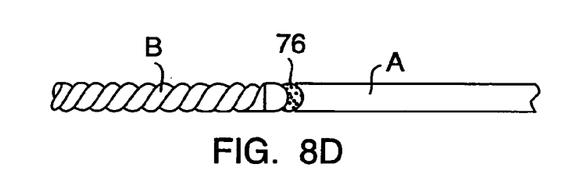
Figure 8E:
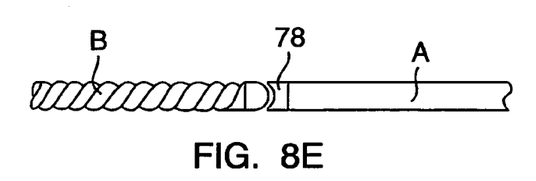

Finally, FIGS. 8A through E illustrate various methods of coupling an insert device A to the blunting device B. FIG. 8A shows a bayonet coupling of a first type wherein the insert device A has a male portion 70 and the blunting device B has a female portion 72. FIG. 8B depicts a bayonet coupling of a second type, which is opposite that depicted in FIG. 8A. FIG. 8C illustrates a frangible connection 74 between the insert device A and the blunting device B. FIG. 8D depicts an adhesive connection between the insert device A and the blunting device B, wherein the adhesive 76 is carried by the blunting device. FIG. 8E illustrates a magnetic connection wherein a magnet 78 is positioned on the blunting instrument A for coupling with a ferromagnetic end portion of an insert member B. These couplers are merely representative and should not be considered limiting. Other couplers include screw and thread, and hook and loop as well as other configurations of those identified above and standard couplers known to those skilled in the art of coupling.

Examples of use of the above blunting devices with a needle and an insert device includes:
using a temperature or pressure probe to assess blood temperature or pressure in an vein or artery;
medical procedures where access to various body cavities, organs, or tissue masses is required;
placement of epidural catheters;
vascular placement of soft-material catheters, such as Bard Access Systems Hohn Catheter;
surgical procedures wherein minimal incisions can be used such as suturing of hard to access tissue, vessels, or organs employing orthopedic or arthroscopic needles; and
biopsy procedures.

Although the present invention has been described in considerable detail with reference to certain preferred versions thereof, other versions are possible, particularly versions wherein the insert device is not coupled to the blunting piece of the blunting device. In addition, although the application has depicted examples for the medical field as related to humans, the invention should not be considered so limited as needles can be used on other animals as well as in non-animal, non-medical situations. Therefore, the spirit and scope of the invention should not be limited to the description of the preferred versions contained herein.

The inventions claimed are as follows:

1. A blunting device for a needle having a bore with an entrance end and an exit end wherein the exit end has a sharp edge for penetrating a body, the blunting device comprising:
    a stopper sized such that the stopper cannot pass through the bore of the needle when entering from the entrance end;
    a blunting piece sized to pass through the bore of the needle from the entrance end to the exit end and prevent impact with the sharp edge, the blunting piece connected to the stopper; and
    a catch operatively associated with the stopper and blunting piece to position a portion of the blunting piece in a position within the exit end, the catch activating upon exiting the exit end.

2. The blunting device of claim 1 further including a coupler operatively associated with the stopper and the blunting piece.

3. The blunting device of claim 2 wherein the coupler comprises a magnet.

4. The blunting device of claim 2 wherein the coupler comprises a bore defined by the blunting piece.

5. The blunting device of claim 1 wherein the stopper is coupled to the blunting piece by a flexible member.

6. The blunting device of claim 5 wherein the blunting piece defines a bore for use as the coupler.

7. The blunting device of claim 6 wherein the catch is a portion of the member extending outwardly from the blunting piece.

8. The blunting device of claim 1 having an insert device coupled thereto.

9. The blunting device of claim 8 wherein the insert device comprises a guide wire.

10. The blunting device of claim 8 wherein the insert device is a medical instrument.

11. A blunting device for a needle having a bore with an entrance end and an exit end wherein the exit end has a sharp edge for penetrating a body, the blunting device comprising:
    a stopper sized such that the stopper cannot pass through the bore of the needle when entering from the entrance end;
    a blunting piece sized to pass through the bore of the needle from the entrance end to the exit end and prevent impact with the sharp edge, the blunting piece connected to the stopper; and
    a coupler operatively associated with the stopper and blunting piece to allow the joining of an insert device with the blunting device.

12. The blunting device of claim 11 further comprising a catch operatively associated with the stopper and the blunting piece for securing the longitudinal position of the blunting piece in the bore of the needle.

13. The blunting device of claim 12 wherein the catch actuates upon exiting the exit end of the needle.

14. The blunting device of claim 11 wherein the coupler comprises a bore defined by the blunting piece.

15. A blunting device for a needle having a bore with an entrance end and an exit end wherein the exit end has a sharp edge for penetrating a body, the blunting device comprising:
    a stopper sized such that the stopper cannot pass through the bore of the needle when entering from the entrance end;
    a blunting piece sized to pass through the bore of the needle from the entrance end to the exit end and prevent impact with the sharp edge, the blunting piece connected to the stopper; and an insert device operatively associated with the stopper and blunting piece.

16. The blunting device of claim 15 further comprising a catch operatively associated with the stopper and blunting piece for securing the longitudinal position of the blunting piece in the exit end of the needle.

* * * * *